(12) United States Patent
Patil et al.

(10) Patent No.: US 8,703,683 B2
(45) Date of Patent: Apr. 22, 2014

(54) POLY (ALKYL EPDXIDES), PROCESS FOR MAKING, AND LUBRICANT COMPOSITIONS HAVING SAME

(75) Inventors: Abhimanyu Onkar Patil, Westfield, NJ (US); Satish Bodige, Wayne, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 697 days.

(21) Appl. No.: 12/766,241

(22) Filed: Apr. 23, 2010

(65) Prior Publication Data

US 2011/0263469 A1    Oct. 27, 2011

(51) Int. Cl.
    *C10M 107/34*     (2006.01)
    *C07C 43/00*     (2006.01)
    *C07C 43/03*     (2006.01)

(52) U.S. Cl.
    USPC .......................... 508/579; 568/671; 568/679

(58) Field of Classification Search
    USPC ................................. 508/579; 568/671, 679
    See application file for complete search history.

(56) References Cited

U.S. PATENT DOCUMENTS

| | | | |
|---|---|---|---|
| 2,782,240 A | | 2/1957 | Hefner et al. |
| 2,965,607 A | * | 12/1960 | Martin et al. .................. 528/112 |
| 3,085,071 A | | 4/1963 | Bailey, Jr. |
| 3,149,178 A | | 9/1964 | Hamilton et al. |
| 3,382,055 A | | 5/1968 | Jacobson et al. |
| 4,481,123 A | | 11/1984 | Hentschel et al. |
| 5,068,487 A | | 11/1991 | Theriot |
| 5,741,946 A | | 4/1998 | Wei |
| 6,087,307 A | | 7/2000 | Kaminski et al. |
| 6,824,671 B2 | | 11/2004 | Goze et al. |
| 2007/0265178 A1 | | 11/2007 | Patil et al. |

(Continued)

FOREIGN PATENT DOCUMENTS

| | | |
|---|---|---|
| JP | 04130188 | 5/1992 |
| JP | 2000325771 | 11/2000 |

(Continued)

OTHER PUBLICATIONS

Kirk-Othmer, Encyclopedia of Chemical Technology, vol. 16, 3rd edition, John Wiley & Sons, pp. 637-653, 1981.

*Primary Examiner* — Prem Singh
*Assistant Examiner* — Vishal Vasisth
(74) *Attorney, Agent, or Firm* — Robert A. Migliorini

(57) ABSTRACT

A process for making a poly(alkyl epoxide). The process has the step of polymerizing one or more alkyl epoxide monomers in the presence of a cationic catalyst according to the following sequences:

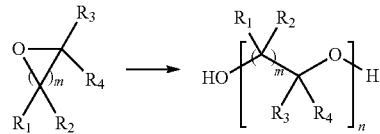

wherein $R_1$, $R_2$, $R_3$, and $R_4$ are hydrogen or alkyl moieties that, taken together, have a total of 1 to 80 carbons; wherein any of $R_1$, $R_2$, $R_3$, and $R_4$ can be linear or branched if it is an alkyl moiety; wherein "m" is an integer from 1 to 4; and wherein "n" is an integer from 2 to 120. There is also another process for making a poly(alkyl epoxide) using an initiator. There are also poly(alkyl epoxides). There is also a lubricant composition having a first lubricant base stock of one or more poly(alkyl epoxides) and a second lubricant base stock different than the first lubricant base stock.

12 Claims, 4 Drawing Sheets

(56) References Cited

U.S. PATENT DOCUMENTS

2008/0177121 A1   7/2008   Wu et al.
2009/0240012 A1*   9/2009   Patil et al. ................ 526/237
2011/0143983 A1*   6/2011   Patil .............................. 508/579

FOREIGN PATENT DOCUMENTS

| WO | 9929743 | 6/1999 |
|---|---|---|
| WO | 2007011973 A1 | 1/2007 |
| WO | 2007/106215 A1 | 9/2007 |

* cited by examiner

POLY (ALKYL EPDXIDES), PROCESS FOR MAKING, AND LUBRICANT COMPOSITIONS HAVING SAME

FIELD

The present disclosure relates to poly(alkyl epoxides) and their polymerization. The present disclosure further relates to the polymerization of alkyl epoxides in the presence of a cationic catalyst. The present disclosure further relates to the polymerization of alkyl epoxides in the presence of a cationic catalyst and an initiator. The present disclosure still further relates to a process for making the lubricant base stock. The present disclosure still yet further relates to a lubricant formulation having poly(alkyl epoxide) polymer therein.

BACKGROUND

Poly(alpha-olefin) (PAOs) fluids are commercially employed as base stocks in lubricant products. PAOs have many advantages compared to conventional mineral oils and Group III/III+ lubricants. More specifically, PAOs have superior VI (viscosity index), low temperature properties (CCS (crankcase simulation), MRV (mini-rotary viscometer), etc.), pour points, and low traction, which translates into better energy efficiency and additive response and complete miscibility in conventional mineral oils. Performance limitations of PAOs include a lack of polarity, which impacts ability to solubilize polar additives, such as antioxidants, anti-rust agents and anti-wear agents. Conventionally, polar organic esters have been added to PAO lubricants to render them compatible. Useful commercial formulations may have 2% or more of such esters in a fully homogeneous lubricant blend. Examples of such esters include, for example, bis-tridecanol adipate and pentaerythritol hexanoate.

Polyalkylene glycol (PAG) fluids have also been employed as lubricant base stocks. Their performance advantages are high VI, good lubricity (in hydrodynamic, mix, and boundary lubrication conditions), and excellent cleanliness. Some grades are even considered acceptable for incidental food contact (H1 grade). Performance limitations include lack of miscibility and compatibility with conventional mineral and hydrocarbon-based lubricants as well as high solubility in water, which results in severe corrosion problem. Some PAGs have paint or seal compatibility problems. The formulation or additive response of PAGs with respect to additives can be unpredictable, rendering them difficult to formulate with.

Other teachings to useful PAO and PAG fluids and processes for making are disclosed in *Synthetics, Mineral Oils, and Bio-Based Lubricants, Chemistry and Technology*, by L. R. Rudnick, CRC Press, © 2006.

It would be desirable to have a process for making poly (alkyl epoxides) that is economical and easy to control. It would further be desirable to have a process for making poly(alkyl epoxides) in which mixtures of α-olefins could be utilized for epoxidation and oligomerization. It would also be desirable to have a process for making poly(alkyl epoxides) employing an initiator for polymerization. It would also be desirable to have poly(alkyl epoxides) that are highly soluble in PAO-type hydrocarbon fluids and that have a base stock that exhibits a low coefficient of friction. It would also be desirable to have a lubricant composition having a base stock of a poly(alkyl epoxide).

SUMMARY

According to the present disclosure, there is provided a poly(alkyl epoxide) of the following structure:

wherein $R_1$, $R_2$, $R_3$, and $R_4$ are hydrogen or alkyl moieties that, taken together, have a total of 1 to 80 carbons; wherein any of $R_1$, $R_2$, $R_3$, and $R_4$ can be linear or branched if it is an alkyl moiety; wherein "m" is an integer from 1 to 4; and wherein "n" is an integer from 2 to 120.

According to the present disclosure, there is provided a process for making a poly(alkyl epoxide). The process has the step of polymerizing one or more alkyl epoxide monomers in the presence of a cationic catalyst according to the following sequence:

wherein $R_1$, $R_2$, $R_3$, and $R_4$ are hydrogen or alkyl moieties that, taken together, have a total of 1 to 80 carbons; wherein any of $R_1$, $R_2$, $R_3$, and $R_4$ can be linear or branched if it is an alkyl moiety; wherein "m" is an integer from 1 to 4; and wherein "n" is an integer from 2 to 120.

According to the present disclosure, there is provided a poly(alkyl epoxide) of the following structure:

wherein $R_1$, $R_2$, $R_3$, and $R_4$ are hydrogen or alkyl moieties that, taken together, have a total of 1 to 80 carbons; wherein any of $R_1$, $R_2$, $R_3$, and $R_4$ can be linear or branched if it is an alkyl moiety; wherein R' is an alkyl moiety, linear or branched, having from 1 to 120 carbons; and wherein "m" is an integer from 1 to 4; and wherein "n" is an integer from 2 to 120.

According to the present disclosure, there is provided another process for making a poly(alkyl epoxide). The process has the step of polymerizing one or more alkyl epoxide monomers in the presence of a cationic catalyst and an initiator according to the following sequence:

wherein $R_1$, $R_2$, $R_3$, and $R_4$ are hydrogen or alkyl moieties that, taken together, have a total of 1 to 120 carbons; wherein any of $R_1$, $R_2$, $R_3$, and $R_4$ can be linear or branched if it is an alkyl moiety; wherein R' is an alkyl moiety, linear or branched, having from 1 to 120 carbons; and wherein "m" is an integer from 1 to 4; and wherein "n" is an integer from 2 to 120.

According to the present disclosure, there is provided a lubricant composition. The composition has a first lubricant base stock of either or both of the aforementioned poly(epoxyalkane) polymers and a second lubricant base stock different than the first lubricant base stock. Preferably, the second base stock is selected from among metallocene based poly-α-olefins, poly-α-olefins, a GTL (gas-to-liquids materials), a Group I base stock, a Group II based stock, a Group III base stock and combinations of the foregoing.

DETAILED DESCRIPTION

All numerical values within the detailed description and the claims herein are modified by "about" or "approximately" the indicated value, and take into account experimental error and variations that would be expected by a person having ordinary skill in the art.

An embodiment of a poly(alkyl epoxide) of the present disclosure is the following structure:

wherein $R_1$, $R_2$, $R_3$, and $R_4$ are hydrogen or alkyl moieties that, taken together, have a total of 1 to 80 carbons; wherein any of $R_1$, $R_2$, $R_3$, and $R_4$ can be linear or branched if it is an alkyl moiety; wherein "m" is an integer from 1 to 4; and wherein "n" is an integer from 2 to 120.

An embodiment of a process for making a poly(alkyl epoxide) of the present disclosure has the step of polymerizing one or more alkyl epoxide monomers in the presence of a cationic catalyst according to the following sequence:

wherein $R_1$, $R_2$, $R_3$, and $R_4$ are hydrogen or alkyl moieties that, taken together, have a total of 1 to 80 carbons; wherein any of $R_1$, $R_2$, $R_3$, and $R_4$ can be linear or branched if it is an alkyl moiety; wherein "m" is an integer from 1 to 4; and wherein "n" is an integer from 2 to 120.

Another embodiment of a poly(alkyl epoxide) of the present disclosure is the following structure:

wherein $R_1$, $R_2$, $R_3$, and $R_4$ are hydrogen or alkyl moieties that, taken together, have a total of 1 to 80 carbons; wherein any of $R_1$, $R_2$, $R_3$, and $R_4$ can be linear or branched if it is an alkyl moiety; wherein R' is an alkyl moiety, linear or branched, having from 1 to 120 carbons; and wherein "m" is an integer from 1 to 4; and wherein "n" is an integer from 2 to 120.

An embodiment for making a poly(alkyl epoxide) of the present disclosure has the step of polymerizing one or more alkyl epoxide monomers in the presence of a cationic catalyst and an initiator according to the following sequence:

wherein $R_1$, $R_2$, $R_3$, and $R_4$ are hydrogen or alkyl moieties that, taken together, have a total of 1 to 120 carbons; wherein any of $R_1$, $R_2$, $R_3$, and $R_4$ can be linear or branched if it is an alkyl moiety; wherein R' is an alkyl moiety, linear or branched, having from 1 to 120 carbons; and wherein "m" is an integer from 1 to 4; and wherein "n" is an integer from 2 to 120.

Initiators useful in an embodiment the process of the present disclosure include alkyl alcohols, such as those of 4 to 120 carbons and preferably 8 to 40 carbons.

'Oxo' alcohols can also be used as initiators (R'—OH). The group of 'oxo' alcohols includes hydrogenation products formed directly from 'oxo' aldehydes obtained by hydroformulations of olefins as well as those from their primarily aldolization or aldol condensation products. Manufacture of 'oxo' alcohols involves catalytic hydrogenation of 'oxo' aldehydes usually either by gas phase with Ni or Cu catalysts or liquid phase with Ni catalysts. The Oxo process is well known in the art and is generally described in detail in Kirk-Othmer, Encyclopedia of Chemical Technology, Volume 16, 3rd ed., John Wiley & Sons, pp. 637-653, 1981.

In the 'oxo' process, olefins are hydroformulated by reaction with carbon monoxide and hydrogen, generally charged as synthesis gas (syn gas) mixtures, in the presence of a cobalt Oxo catalyst in dissolved form to form a mixture of Oxo aldehydes and alcohols. This Oxo reaction is typically carried out at syn gas pressures of from 10.33 MPa to 31.00 MPa (1500 to 4500 psig) and at temperatures of from 65° C. to 230° C. Thereafter, the product mixture containing the alcohols and aldehydes is recovered and can be treated by known means to hydrogenate the aldehydes to form additional quantities of the corresponding alcohols.

The $C_8$-$C_{13}$ 'oxo' alcohols obtained from olefin oligomers (e.g., isoheptanes, diisobutenes, tripropenes) and from cracked olefins are useful as initiators for epoxyalkane polymerization. Industrially available branched and unbranched higher olefins are important feedstocks for the manufacture of $C_{12}$-$C_{19}$ alcohols after hydroformulation and hydrogenation. These alcohols, in turn, can be used as initiators.

Other kind of alcohols include that can be prepared from unhydrogenated PAO (PAO with terminal double bond) or of other hydrocarbon macromers, such as polyethylene (PE), polypropylene (PP), ethylene propylene (EP), ethylene butylene (EB), polyisobutylene (PIB), and poly-n-butylene (PNB) macromers.

As used herein, the term "macromer" is defined as a polymeric structure that contains terminal unsaturation (terminal double bond), e.g., ethylene monomer units, propylene monomer units, other alpha-olefin monomer units, and combinations thereof. A macromer is a polymer with a relatively low molecular weight with vinyl, vinylene, or vinylidene terminal olefin. For example, a macromer can be a polymer having a weight average molecular weight ($M_w$) of 20,000 or less, or, more narrowly, 5,000 or less or 2,000 or less. Vinyl-terminated polymers or oligomers, homopolymers and copolymers synthesized from two or more monomers. Preparation of vinyl-containing macromers is described in U.S. Pat. No. 6,555,635 B2, which is incorporated herein by reference in its entirety.

Preparation of Vinyl-Containing Stereospecific Polypropylene macromers and their manufacture is described in WO 9929743, which is incorporated herein by reference in its entirety. The macromer can also be a low molecular weight oligomer of α-olefin that has double bond. For example, a dimer of 1-decene can be prepared via metallocene catalyst.

These macromers are known to be useful for post-polymerization modification using 'oxo' chemistry, hydroboration followed by oxidation chemistry, carbonyl-ene chemistry to obtain alcohol functional material that can be used as an initiator in process of the present disclosure.

Examples of useful initiators include, for example, 2-octyl-1-dodecanol, PAO-OH, metallocene-based PAO-OH, polyethylene monoalcohol (Aldrich CAS #71750-71-5, $M_n$~460 or $M_n$~700), polypropylene-OH, ethylene-butylene copolymer-OH, and long-chain fatty alcohols. A preferred initiator is 2-octyl-1-dodecanol.

The poly(alkyl epoxide) is produced by cationic or acid-catalyzed polymerization. Lewis acid catalysts are preferred. Examples of Lewis acid catalysts include metal and metalloid halides conventionally used as Friedel-Crafts catalysts, such as $AlCl_3$, $BF_3$, $AlBr_3$, $TiCl_3$, and $TiCl_4$ either alone or with a protic promoter. Solid Lewis acid catalysts, such as synthetic or natural zeolites; acid clays; polymeric acidic resins; amorphous solid catalysts, such as silica-alumina; and heteropoly acids, such as the tungsten zirconates, tungsten molybdates, tungsten vanadates, phosphotungstates and molybdotungstovanadogermanates (e.g., $WOx/ZrO_2$, $WOx/MoO_3$), may also be used. In general, the acid catalyst used in the polymerization process is 0.1 to 30 wt % and preferably 0.2 to 5 wt % based on total feed.

Preferred Lewis acid catalysts are the metal and metalloid halides. The catalysts most preferred in conventional PAO oligomerization processes are aluminum trichloride and boron trifluoride. Boron trifluoride is typically used in combination with a protic promoter. Promoters are well known in $BF_3$-catalyzed olefin oligomerization processes include water, alcohols, such as the lower ($C_1$-$C_6$) alkanols, methanol, ethanol, isopropanol, and butanol; acids; organic acids, including carboxylic acids such as acetic acid, propionic acid, and butanoic acid; anhydrides of organic acids such as acetic anhydride; inorganic acids, such as phosphoric acid, and as further described in U.S. Pat. No. 3,149,178; esters, such as ethyl acetate, and as further described in U.S. Pat. No. 6,824,671; alcohol alkoxylates, such as glycol ethers, e.g., ethylene glycol monomethyl ether (2-methoxyethanol) and propylene glycol monoethyl ether and ethoxylates derived from mixed $C_2$ to $C_{24}$, preferably $C_2$ to $C_{18}$, and most preferably $C_6$ to $C_{12}$ straight chain alcohols, and as further described in U.S. Pat. No. 5,068,487; ethers, such as dimethyl ether, diethyl ether and methyl ethyl ether; ketones; aldehydes; and alkyl halides. Protic promoters form a catalyst complex with the boron trifluoride, and such complex serves as a catalyst for the oligomerization. The complex usually contains an excess of boron trifluoride, which is adsorbed in the mixture.

Solvents or diluents may be used in the Lewis acid catalyzed polymerization. If the catalyst system being used is a liquid, this may also function as the solvent or diluent for the reaction so that no additional solvent or diluent may be required. Additional liquids that are non-reactive to the selected catalyst system may be used as needed to control viscosity of the reaction mixture or to carry off heat of reaction by evaporation with reflux of the condensed vapor, if desired. Hydrocarbons such as alkanes and aromatics, e.g., hexane and toluene, are suitable for this purpose. Thus, a light alpha-olefin oligomer reactant, either alone or with additional alpha-olefin co-feed, may be oligomerized directly in the presence of the catalyst system with or without the addition of solvent or diluent. The reactions will normally be carried out in a closed environment if gaseous catalysts such as boron trifluoride are used. Such reactions are usually carried out under an inert atmosphere, e.g., nitrogen.

The temperature of the Lewis acid-catalyzed polymerization reactions can usefully vary in practical operation from −90° C. to 300° C. and preferably from −30° C. to 125° C. Reaction time can vary from 1 minute to 36 hours and preferably from 1 hour to 24 hours. The system may operate under atmospheric pressure as the system typically exhibits low vapor pressures at normal processing temperatures. The system may, however, be operated under mild pressure if it is desired to maintain a closed reaction environment, e.g., under autogenous pressure. When using a solid Lewis acid as the catalyst, the polymerization will normally be carried out using a fixed bed of the catalyst in a downflow mode, although alternative forms of operation, e.g., in a stirred tank reactor, are possible.

Following completion of the polymerization reaction, the catalyst activity may be quenched by addition of water or a dilute aqueous base, such as a 5 wt % NaOH solution. The organic layer may be separated and distilled to remove components other than the base stock. When promoted $BF_3$ catalyst is used, the gaseous $BF_3$ and promoter may be recycled if not deactivated at the end of the reaction. When a solid catalyst is used, a simple filtration is all that is needed to separate the catalyst from the polymer product if the reaction has not been carried out in a fixed bed. The polymer product may then be fractionated to remove any unreacted light olefin and the polymer in the desired boiling range, and, optionally, sent for hydrogenation to remove any residual unsaturation that may be present in the product.

The molecular weight of the poly(alkyl epoxide) typically ranges from 200 to 20,000, typically from 300 to 10,000, and most typically from 350 to 7,500. Higher molecular weights and corresponding viscosities may be achieved by suitable choice of reaction conditions. Values of the polydispersity index (PDI) are typically from 1 to 3.

Alkyl epoxides useful as monomers in the process of the present disclosure include those having one or more alkyl moieties that have 1 to 80 carbons, preferably 4 to 40 carbons, and more preferably 8 to 20 carbons and can be linear or branched in structure. The epoxide moiety takes the form of a 3 to 6 carbon ring. Three-member rings are preferred.

Alkyl epoxides can be prepared by epoxidation of olefins. Olefins can be linear or branched from 4 to 20 carbons. The olefins can be single or mixed such as mixed $C_4$ olefins. The mixed $C_4$ olefins include raffinate I (Raff-I) and raffinate II (Raff-II). Typical Raff-I and Raff-II composition percentages are as follows: Raff-I gas mixture, which contained 31.0% of isobutylene, 42.94% of 1-butene, 12.5% of 2-butene, 12.5% of trans-2-butene and 1.06% of butadiene. RAF-II mixture (mole % cis 2-butene: 17%, trans 2-butene 17%, isobutylene 5.51%, 1,3-butadiene 5237 ppm and remaining 1-butene). Raffinate-1 or -2 (Raff-1 or Raff-2, respectively) are per se well known. See, for instance, WO2007/106215. Although one skilled in the art knows that such amounts can vary depending on the source of the feed: Other mixtures that can be used as a feed for epoxidation can come from light olefins from fluidized catalytic cracking ("FCC"), propylene/$C_4$ olefins, such as n-butenes and isobutylene, and $C_4$ olefin streams from methanol-to-olefin ("MTO") processes.

Olefins are epoxidized using an epoxidation catalyst to produce epoxidized product. Epoxidation of the olefin materials can be affected using a peracid, such as performic acid, perbenzoic acid or m-chloroperbenzoic acid, as the oxidizing agent. The oxidation reaction can be performed using a pre-formed peracid to affect the epoxidation, or the peracid can be generated in-situ, for example by the addition of formic acid and hydrogen peroxide to produce performic acid. Formic acid can be added in a molar ratio to the olefin double bonds of from 10:1 to 30:1. Hydrogen peroxide can be added to the reaction mixture in a molar ratio to the olefin double bonds of from 1.01:1 to 5:1. Addition of both formic acid and $H_2O_2$ to the reaction mixture results in the in-situ formation of performic acid as an epoxidizing agent. Typically, the epoxidation is conducted at a temperature ranging from $-10°$ C. to $100°$ C., preferably from $30°$ C. to $70°$ C. Suitable reaction times will generally range from 0.1 hour to 36 hours, such as from 1 hour to 24 hours. Epoxidation reactions can provide conversion from 50 to 100% of the double bonds into oxirane groups.

The epoxidation reaction is generally carried out in a liquid reaction medium. The reaction medium can comprise only the reactants essentially utilized in the process. More conventionally, however, the liquid reaction medium will comprise a suitable reaction solvent in which the reactants and catalyst materials can be dissolved, suspended or dispersed. Suitable reaction solvents include organic liquids that are inert in the reaction mixture. By "inert" is meant that the solvent does not deleteriously affect the oxidation reaction. Suitable inert organic solvents include aromatic hydrocarbons such as benzene, toluene, xylenes, benzonitrile, nitrobenzene, anisole, and phenyl nonane; saturated aliphatic hydrocarbons having from 5 to 20 carbons, such as pentane, hexane, and heptane; adiponitrile; halogenated hydrocarbons such as methylene chloride, 1,2-dichloroethane, chloroform, carbon tetrachloride and the like; non-fluorinated, substituted saturated aliphatic and/or aromatic hydrocarbons having from 1 to 20 carbons, including those selected from the group consisting of alcohols such as methanol, propanol, butanol, isopropanol, and 2,4-di-t-butylphenol; ketones such as acetone; carboxylic acids such as propanoic acid and acetic acid; esters such as ethyl acetate, ethyl benzoate, dimethyl succinate, butyl acetate, tri-n-butyl phosphate, and dimethyl phthalate; ethers, such as tetraglyme; and mixtures thereof.

One type of epoxidation of olefins involves reaction of the material with a peracid, such as performic acid or m-chloroperbenzoic acid, to provide an epoxidized material having oxirane rings formed at the sites of the residual double bonds within the molecule. Catalytic epoxidation alternatives using hydrogen peroxide as an oxidizing agent instead of peracids can be used to epoxidize some unsaturated materials. Catalysts based on Ti, V, Mo, W and Re metal complexes are known to promote alkene epoxidation with $H_2O_2$. Some notable effective epoxidation catalysts for use with hydrogen peroxide include titanium silicates, peroxophosphotungstates, manganese triazocyclononane, and methylrhenium trioxide.

Epoxidized products of other one or more olefins include 1,2-epoxyoctane, 1,2-epoxynonane, 1,2-epoxydecane, 1,2-epoxydodecane, 1,2-epoxytetradecene, and 1,2-epoxyoctadecane.

The poly(alkyl epoxide) is useful use as a lubricant base stock or a functional fluid and preferably has a $100°$ C. kinematic viscosity of 1.5 cSt to 3000 cSt according to ASTM D445 method. The polymer has a $40°$ C. kinematic viscosity of 3 to 15000 cSt. Preferred polymers exhibit a high viscosity index (VI). The VI typically ranges from 70 to 300 depending on viscosity, type and number of monomeric units, method of synthesis, chemical composition, and the like. Pour points are generally below $-5°$ C. even in the case of the higher molecular weight oligomers with viscosities ($100°$ C.) of 20 cSt or higher. Pour points (ASTM D97 or equivalent) generally range between $-20°$ C. and $-55°$ C. and usually below $-25°$ C. Product viscosity may vary in view of factors such as polymerization conditions, such as reaction temperature and reaction time. Higher temperatures and reaction times may result in higher molecular weight/higher viscosity products. The lubricant fraction of the product will typically be a 4 cSt to 3000 cSt ($100°$ C.) material, but low viscosity products 1.5 cSt to 40 cSt ($100°$ C.) may also be obtained for use in lubricants in which a low viscosity base stock is desired.

An advantage of the process of the present disclosure is that it can be employed using alkyl epoxide monomers manufactured from raffinate feedstreams of mixed $\alpha$-olefins, such as 1-butene and 2-butene.

The poly(alkyl epoxide) polymer may be admixed with other lubricant base stocks with which it is soluble or miscible. Useful blending base stocks include metallocene PAOs, PAOs, GTL (gas-to-liquid materials), Group I, Group II, and Visom (Group III) base stocks. PAO base stocks are disclosed, for example, in U.S. Published Application No. 2008/0177121 A1, which is incorporated herein by reference. GTL base stocks are disclosed, for example, in U.S. Published Application No. 2007/0265178 A1, which is incorporated herein by reference. The polymer may be admixed with other (different) lubricant base stocks in any proportion, such as 1 wt % to 99 wt % polymer and 99 wt % to 1 wt % other lubricant base stocks (and any proportion in between) based on the total weight thereof. Preferred blends have 0.5 wt % polymer and 99.5 wt % other lubricant base stocks, more preferably 5 wt % to 95 wt %, and most preferably 20 wt % to 80 wt % based on the total weight thereof.

For automotive engine lubricant formulations, it is generally preferred to have lower viscosity fluids, e.g., below 10 cSt. Lower viscosity is known to impart lower viscous drag and, thus, afford better energy efficiency or fuel economy. Both low viscosity and high viscosity fluids are useful in industrial lubricant formulations to yield different ISO vis grad lubricants. For industrial lubricant formulations, it is generally important to use fluids of high VI and high hydrolytic stability.

For both engine and industrial lubricant application, it is important to have a lubricant formulation with a low friction coefficient. Fluids with low friction coefficients exhibit low frictional loss during lubrication. Low frictional loss is critical for improved energy or fuel efficiency of formulated lubricants.

Friction coefficients can be measured by a High Frequency Reciprocating Rig (HFRR) test. The test equipment and procedure are similar to the ASTM D6079 method except the test oil temperature is raised from 32° C. to 195° C. at 2° C./minute, 400 g load, 60 Hz frequency, 0.5 mm stroke length or 400 g load, and 60 Hz frequency at constant temperature, such as 100° C. or 60° C. The test can measure average friction coefficient and wear volume.

The following examples are illustrative of the disclosure and are not to be construed as limiting.

EXAMPLES

Example 1

Polymerization of 1,2-Epoxybutane

Charged 1,2-epoxybutane (5.7 grams, 0.08 mole) in to three-necked round bottom flasks under $N_2$. Slowly added anhydrous $AlCl_3$ (0.32 grams, 0.0024 mole) in 2 hours by maintaining the reaction temperature below −5° C. After addition, the reaction mixture was stirred for 2 hours at −5° C. The reaction was stopped by adding 50 ml water and 75 ml MTBE (methyl tert-butyl ether). The MTBE layer was washed with water (2×75 ml) and (1×75 ml) brine until the aqueous layer attained a pH of ~7. The MTBE layer was separated and dried over anhydrous $MgSO_4$ and filtered. The low boiling MTBE was removed by using a rotary evaporator at 95° C. under house vacuum. The final product yield was 21%.

Figure 1:
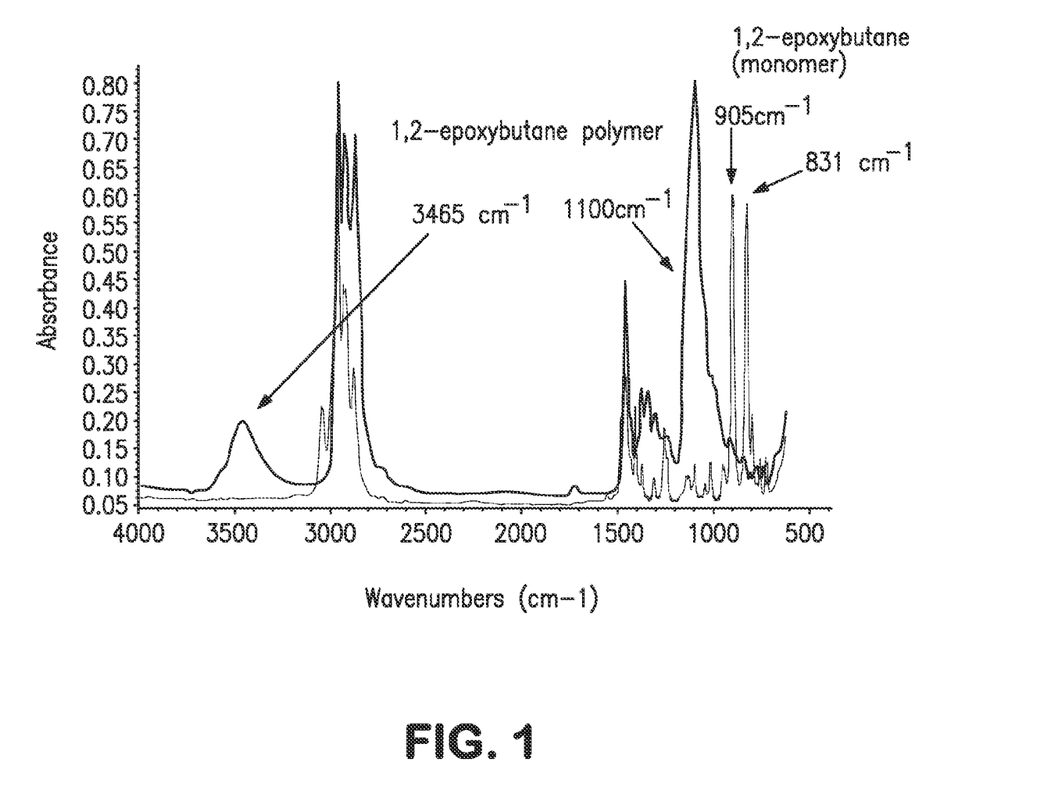
FIG. 1 is a depiction of an IR spectra of a 1,2-epoxybutane monomer and a 1,2-epoxybutane polymer of the present disclosure of Example 1.

FIG. 1 shows an IR spectra of 1,2-epoxybutane monomer and a 1,2-epoxybutane polymer. The IR spectrum of monomer shows characteristic epoxide absorption peaks at 905 $cm^{-1}$ and 831 $cm^{-1}$. The IR spectrum of the polymer shows disappearance of the peaks at 905 $cm^{-1}$ and 831 $cm^{-1}$ and new absorption peaks at 1100 $cm^{-1}$ (polyether) and 3465 $cm^{-1}$ (hydroxyl peak) appeared in the polymer spectrum. The $^1H$ NMR spectrum showed a broad doublet at 0.86-0.96 ppm (—$CH_3$), a mutiplet at 1.54 ppm (—$CH_2$—) and a complex mutiplet center at 3.37-3.40 ppm (—$CH_2$—O, —CH—O), which suggests the formation of a homopolymer of epoxy butane. Thus, both IR and NMR analysis suggest the formation of 1,2-epoxybutane homopolymer. The product was soluble in PAO 6.

Example 2

Homopolymerization of 1,2-Epoxyoctane

Charged $AlCl_3$ (1.03 grams, 0.0078 mole) and 5 ml decane in three-necked round bottom flasks under $N_2$ with a mechanical stirrer. Slowly added 1,2-epoxyoctane (10 grams, 0.0781 mole) with an additional funnel at room temperature. After addition, the reaction mixture was stirred for 72 hours. Stopped the reaction by adding 50 ml water and 75 ml MTBE. The MTBE layer was washed with water (2×75 ml) and (1×75 ml) brine until the aqueous layer attained a pH of ~7. The separated MTBE layer was then dried over anhydrous $MgSO_4$ and filtered. The low-boiling MTBE was removed by using a rotary evaporator at 60° C. The high-boiling (1-decane and unreacted 1,2-epoxyoctane) component with an air bath oven at 160° C.-170° C. under vacuum. The final product yield was 50%.

Figure 2:
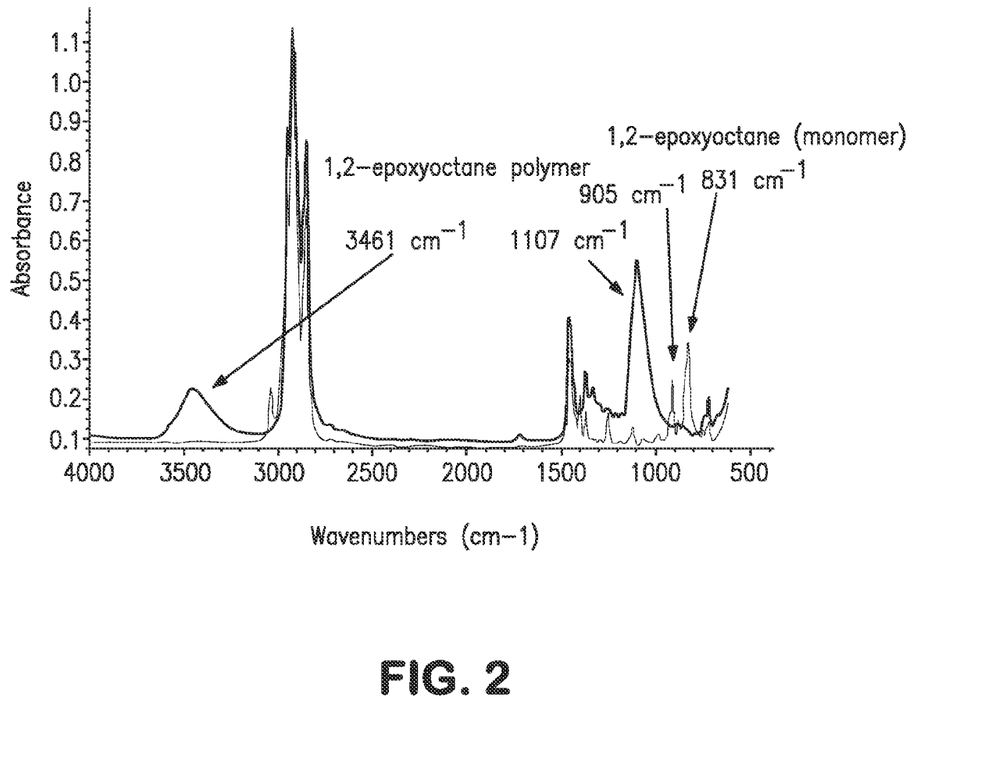
FIG. 2 is a depiction of an IR spectra of a 1,2-epoxyoctane monomer and a 1,2-epoxyoctane polymer of the present disclosure of Example 2.

The polymer product was characterized using IR, NMR and GPC. FIG. 2 shows an IR spectra of 1,2-epoxyoctane monomer and 1,2-epoxyoctane polymer. An IR spectrum of monomer shows characteristic epoxide absorption peaks at 905 $cm^{-1}$ and 831 $cm^{-1}$. An IR spectrum of the polymer product shows disappearance of the peaks at 905 $cm^{-1}$ and 831 $cm^{-1}$ and new absorption peaks at 1107 $cm^{-1}$ (polyether) and 3461 $cm^{-1}$ (hydroxyl peak). The $^1H$ NMR spectrum of the product shows a singlet at 0.848 ppm (—$CH_3$), a broad mutiplet at 1.24 ppm-1.51 ppm (—$CH_2$—$CH_2$—$CH_2$—$CH_2$—$CH_2$—) and a complex mutiplet center at 3.49 ppm (—$CH_2$—O, —CH—O), which suggests formation of a homopolymer of epoxy octane. Thus, both IR and NMR analysis suggest the formation of 1,2-epoxyoctane homopolymer. The GPC gave a $M_n$ of 662, a $M_w$ of 719 using polystyrene standards.

The IR spectrum of 1,2-epoxybutane polymer and 1,2-epoxyoctane polymer, it was found that the IR spectra are similar and show characteristic polyether absorption peaks (1100 $cm^{-1}$ and 1107 $cm^{-1}$) and hydroxyl peaks (3465 $cm^{-1}$ and 3461 $cm^{-1}$). IR spectrum of 1,2-epoxyoctane polymer shows an additional absorption peak at 725 $cm^{-1}$ due to an alkyl chain of $C_6$ carbons. The product was soluble in PAO 6.

Lube Properties of Base Stocks

The kinematic viscosity (Kv) of the liquid product was measured using ASTM standard D 445 and reported at temperatures of 100° C. (Kv at 100° C.) and/or 40° C. (Kv at 40° C.). The viscosity index (VI) was measured according to ASTM standard D 2270 using the measured kinematic viscosities for each product. The viscosity of the product at 100° C. and at 40° C. is shown in Table 1.

TABLE 1

Lube Properties of Base Stocks

| Sample # | $Kv_{100}$ | $Kv_{40}$ | Viscosity Index (VI) |
|---|---|---|---|
| Example 1 | 2.7 | 15.4 | — |
| Example 2 | 5.1 | 32.5 | 81 |
| PAO 6 | 5.8 | 31 | 138 |

Friction Coefficients of Base Stocks

Lubricant fuel/energy efficiency has been identified as a important feature for future lubricants. To provide step-out fuel economy while maintaining or improving other performance features for lubricants, base stocks with lower friction coefficients are needed. The friction coefficient was measured by HFRR (high frequency reciprocating rig) (Speed: 0.1 m/s (60 Hz), temperature of 100° C., pressure of 1 GPa (500 grams), and duration of 4 hours. The results are shown in Table 2. The friction coefficients of fluids from Example 1 and Example 2 were substantially lower than hydrocarbon fluids like PAO 6. The substantial difference in friction coefficient reflects the energy efficiency of the base stock, The product was soluble in PAO 6.

TABLE 2

The Friction Coefficient of Base Stocks

| Sample # | Friction Coefficient (FC) |
|---|---|
| Example 1 | 0.08 |
| Example 2 | 0.09 |
| PAO 6 | 0.19 |

Example 3

Polymerization of 1,2-Epoxybutane Using $C_{20}$-Alcohol (2-octyl-1-dodecanol) as an Initiator Charged 2-octyl-1-dodecanol (11.92 grams, 0.04 mole) and anhydrous $AlCl_3$ (2.66 grams, 0.02 mole) in three-necked round bottom flasks under $N_2$ with mechanical stirring. Slowly added 1,2-epoxybutane (11.5 grams, 0.16 mole) with an additional funnel at room temperature. After addition, the reaction mixture was stirred for 72 hours. Stopped the reaction by adding 100 ml water and 250 ml MTBE. The MTBE layer was washed with water (3×100 ml) and (1×100 ml) brine until the aqueous layer attained a pH of ~7. Then the separated MTBE layer was dried over anhydrous $MgSO_4$ and filtered. The low boiling (MTBE and 1,2-epoxybutane) was removed by using a rotary evaporator at 60° C. The high boiling 1,2-octyl-1-dodecanol removed with an air bath oven at 210° C. under vacuum. The final product yield was 45%.

Figure 3:
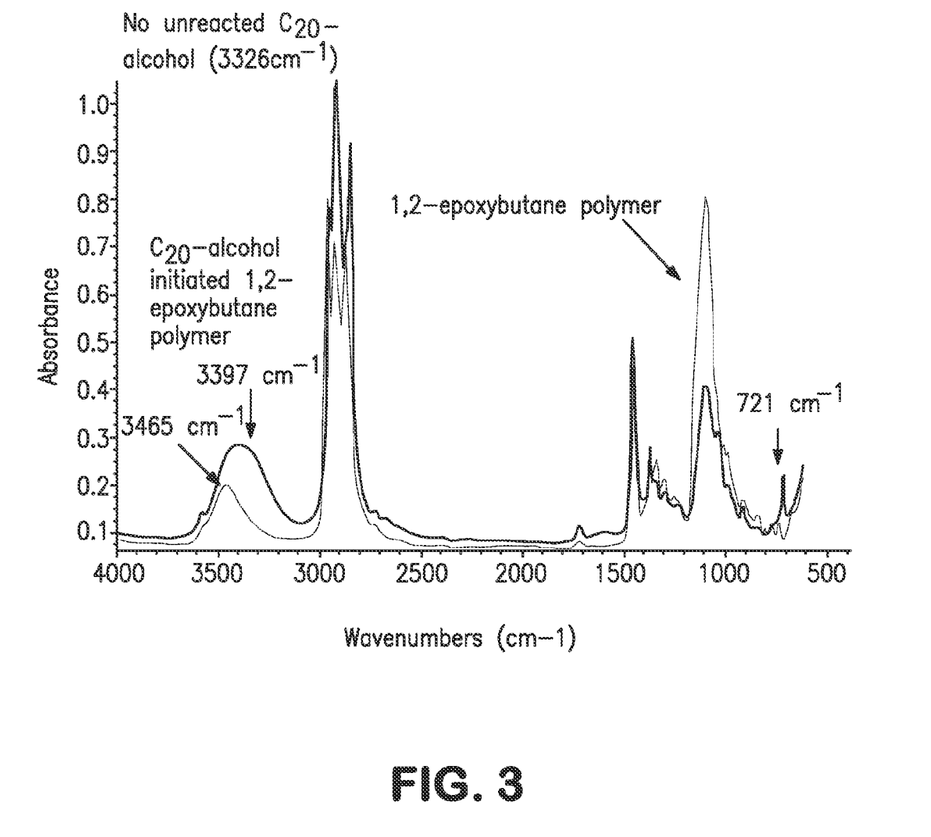
FIG. 3 is a depiction of an IR spectra of a 1,2-epoxybutane polymer of the present disclosure of Example 1 and a 1,2-epoxybutane polymer the present disclosure of prepared using a $C_{20}$ alcohol as an initiator in Example 3.

The polymer was characterized using IR, NMR and GPC. FIG. 3 shows the IR spectra of the 1,2-epoxybutane polymer of Example 1 and the 1,2-epoxybutane polymer prepared using $C_{20}$ alcohol as initiator in Example 3. The respective IR spectra are similar to each other as expected showing characteristic polyether absorption peaks (1110 $cm^{-1}$). The hydroxyl peak is, however, shifted in $C_{20}$ alcohol-initiated 1,2-epoxybutane polymer (3395 $cm^{-1}$ vs. 3465 $cm^{-1}$). The IR spectrum of $C_{20}$ alcohol-initiated 1,2-epoxybutane polymer shows addition absorption peak at 721 $cm^{-1}$ due to the alkyl chain of $C_{20}$ carbons. The spectrum suggests that alcohol is incorporated in the polymer. The $^1H$ NMR spectrum of the product shows a broad doublet at 0.862 ppm (—$CH_3$), a broad mutiplet of epoxy and $C_{20}$ alkyl chain at 1.230 ppm, and a complex mutiplet center at 3.35-3.52 ppm (—$CH_2$—O, —CH—O), suggests the formation alkyl alcohol-initiated 1,2-epoxybutane polymer. Thus, both IR and NMR analysis suggest the formation of alcohol-initiated 1,2-epoxybutane homopolymer. The GPC gave $M_n$ 577, $M_w$ 598 using polystyrene standards.

Example 4

Polymerization of 1,2-Epoxyoctane Using $C_{20}$-Alcohol (2-octyl-1-dodecanol) as Initiator Charged 2-octyl-1-dodecanol (5.96 grams, 0.02 mole) and anhydrous $AlCl_3$ (1.33 grams, 0.01 mole) in 25 ml methylene chloride containing three-necked round bottom flasks under $N_2$ with mechanical stirring. Slowly added 1,2-epoxyoctane (10.24 grams, 0.08 mole) with an additional funnel at room temperature. After addition, the reaction mixture was stirred for 72 hours. Stopped the reaction by adding 50 ml water and 250 ml methylene chloride (MC). The MC layer was washed with water (2×75 ml) and (1×75 ml) brine until the aqueous layer attained a pH of ~7. Then the separated MC layer was dried over anhydrous $MgSO_4$ and filtered. The low boiling MC was removed by using a rotary evaporator at 60° C. The high boiling 1,2-epoxyoctane and 2-octyl-1-dodecanol was removed with an air bath oven at 210° C. under vacuum. The final product yield was 34%.

Figure 4:
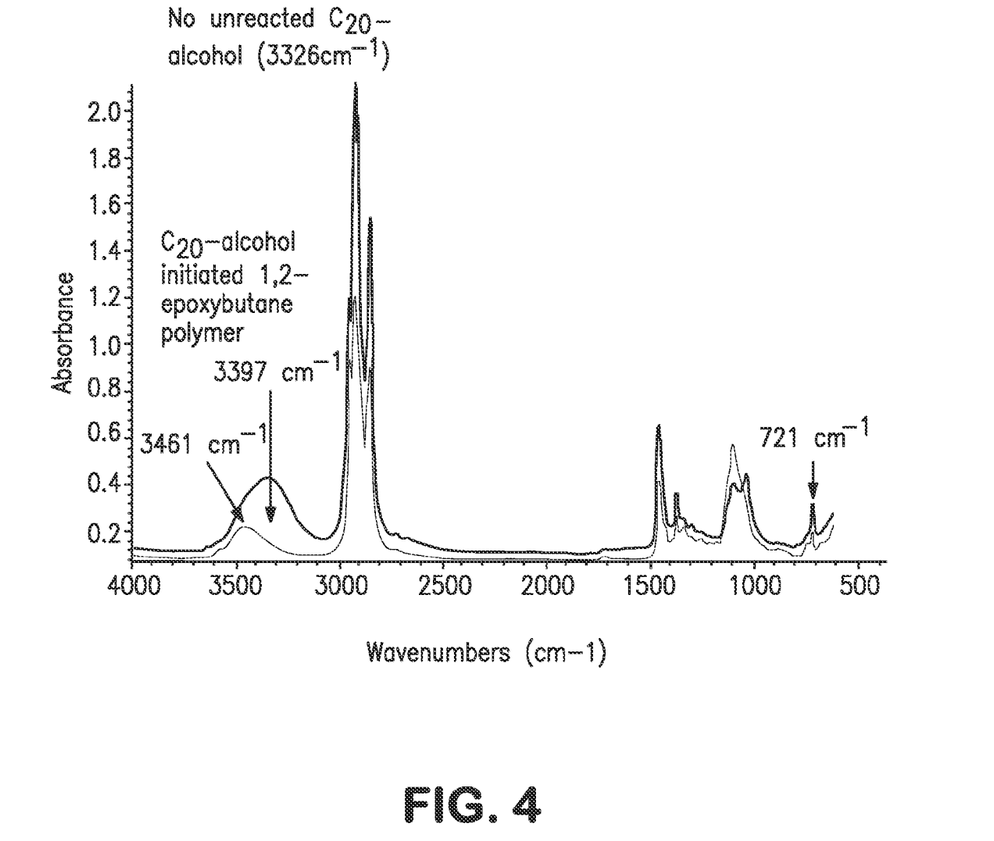
FIG. 4 is a depiction of an IR spectra of a 1,2-epoxyoctane polymer of the present disclosure of Example 2 and a 1,2-epoxyoctane polymer the present disclosure of prepared using a $C_{20}$ alcohol as an initiator in Example 4.

FIG. 4 shows an IR spectra of the 1,2-epoxyoctane polymer of Example 2 and the 1,2-epoxyoctane polymer product prepared using $C_{20}$ alcohol as an initiator in Example 4. The respective IR spectra are similar to each other as expected showing characteristic polyether and hydroxyl peaks. The IR spectrum of $C_{20}$ alcohol-initiated 1,2-epoxyoctane polymer shows an addition absorption peak at 720 $cm^{-1}$ due to the alkyl chain. The product IR analysis suggests the formation of alkyl alcohol-initiated 1,2-epoxyoctane polymer. The $^1H$ NMR spectrum of the product showed a singlet at 0.862 ppm (—$CH_3$), a broad mutiplet of epoxy and $C_{20}$ alkyl chain at 1.230 ppm, and a complex multiplet center at 3.35-3.51 ppm (—$CH_2$—O, —CH—O), which suggests the formation an alkyl alcohol-initiated 1,2-epoxyoctane polymer. Thus, both IR and NMR analysis suggest the formation of alcohol-initiated 1,2-epoxyoctane homopolymer. The GPC gave $M_n$ 574, $M_w$ 603 using polystyrene standards.

Lube Properties of Base Stocks

The kinematic viscosity (Kv) of the liquid product was measured using ASTM standard D 445 and reported at temperatures of 100° C. (Kv at 100° C.) or 40° C. (Kv at 40° C.). The data is shown in Table 3.

TABLE 3

Lube Properties of Base Stocks

| Sample # | $Kv_{100}$ | $Kv_{40}$ |
|---|---|---|
| Example 3 | 3.67 | 23.86 |
| Example 4 | 4.04 | 29.48 |
| PAO 6 | 5.8 | 31 |

The epoxyalkane polymer was soluble with mPAOs, PAOs, GTL, Visom (Gr. III) base stocks. These fluids as such or their blends can be used as lube base stocks.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances that fall within the scope of the appended claims.

Friction Coefficients of Base Stocks

Lubricant fuel/energy efficiency has been identified as an important feature for future lubricants. To provide step-out fuel economy while maintaining or improving other performance features for lubricants, base stocks with lower friction coefficients are needed. The friction coefficient was measured by HFRR (high frequency reciprocating rig) (Speed: 0.1 m/s (60 Hz), temperature of 100° C., pressure of 1 GPa (500 grams), and duration of 4 hours. The results are shown in Table 4.

The friction coefficients of fluids from Example 3 and Example 4 were substantially lower than for PAO 6. The substantial difference in friction coefficient reflects the energy efficiency of the base stock. The product was soluble in PAO 6.

TABLE 4

The Friction Coefficient of Base Stocks

| Sample # | Friction Coefficient (FC) |
|---|---|
| Example 3 | 0.10 |
| Example 4 | 0.10 |
| PAO 6 | 0.19 |

The Applicants have attempted to disclose all embodiments and applications of the disclosed subject matter that could be reasonably foreseen. However, there may be unforeseeable, insubstantial modifications that remain as equivalents. While the present disclosure has been described in conjunction with specific, exemplary embodiments thereof, it is evident that many alterations, modifications, and variations will be apparent to those skilled in the art in light of the foregoing description without departing from the spirit or scope of the present disclosure. Accordingly, the present disclosure is intended to embrace all such alterations, modifications, and variations of the above detailed description.

All patents, test procedures, and other documents cited herein, including priority documents, are fully incorporated by reference to the extent such disclosure is not inconsistent with this disclosure and for all jurisdictions in which such incorporation is permitted.

When numerical lower limits and numerical upper limits are listed herein, ranges from any lower limit to any upper limit are contemplated. All numerical values within the detailed description and the claims herein are modified by "about" or "approximately" the indicated value, and take into account experimental error and variations that would be expected by a person having ordinary skill in the art.

What is claimed is:

1. A process for making a poly(alkyl epoxide), comprising: polymerizing one or more alkyl epoxide monomers in the presence of a Lewis acid catalyst according to the following sequence:

wherein at least one of $R_1$ or $R_2$ and at least one of $R_3$ or $R_4$ are an alkyl moiety and wherein $R_1$, $R_2$, $R_3$, and $R_4$ are hydrogen or alkyl moieties that, taken together, have a total of 1 to 80 carbons; wherein any of $R_1$, $R_2$, $R_3$, and $R_4$ can be linear or branched if it is an alkyl moiety; wherein "m" is 1; and wherein "n" is an integer from 2 to 120, wherein the poly(alkylepoxide) has a Viscosity Index ranging from 70 to 81.

2. The process of claim 1, wherein the Lewis acid is selected from the group consisting of selected from the group consisting of $AlCl_3$, $BF_3$, $AlBr_3$, $TiCl_3$, and $TiCl_4$ either alone or with a protic promoter.

3. The process of claim 1, wherein the Lewis acid is selected from the group consisting of a synthetic or natural zeolites, an acid clay, a polymeric acidic resin, an amorphous solid catalyst, a heteropoly acid, a tungsten zirconate, a tungsten molybdate, a tungsten vanadate, a phosphotungstate, and a molybdotungstovanadogermanate.

4. The process of claim 1, wherein the one or more alkyl epoxides is selected from the group consisting of ethylene oxide, 1,2-epoxybutane, 1,2-epoxyoctane, and 1,2-epoxydecane.

5. The process of claim 1, wherein the polymerizing is carried out at a temperature of –30° C. to 125° C.

6. The process of claim 1, wherein the polymerizing is carried for a time of 1 hour to 24 hours.

7. A process for making a poly(alkyl epoxide) comprising polymerizing one or more alkyl epoxide monomers in the presence of a Lewis acid catalyst and an initiator of R'OH according to the following sequence:

wherein at least one of $R_1$ or $R_2$ and at least one of $R_3$ or $R_4$ are an alkyl moiety and wherein $R_1$, $R_2$, $R_3$, and $R_4$ are hydrogen or alkyl moieties that, taken together, have a total of 1 to 80 carbons; wherein any of $R_1$, $R_2$, $R_3$, and $R_4$ can be linear or branched if it is an alkyl moiety; wherein "m" is 1; and wherein "n" is an integer from 2 to 120, wherein the poly(alkylepoxide) has a Viscosity Index ranging from 70 to 81.

8. The process of claim 7, wherein the Lewis acid is selected from the group consisting of selected from the group consisting of $AlCl_3$, $BF_3$, $AlBr_3$, $TiCl_3$, and $TiCl_4$ either alone or with a protic promoter.

9. The process of claim 7, wherein the Lewis acid is selected from the group consisting of a synthetic or natural zeolites, an acid clay, a polymeric acidic resin, an amorphous solid catalyst, a heteropoly acid, a tungsten zirconate, a tungsten molybdate, a tungsten vanadate, a phosphotungstate, and a molybdotungstovanadogermanate.

10. The process of claim 7, wherein the one or more alkyl epoxides is selected from the group consisting of ethylene oxide 1,2-epoxybutane, 1,2-epoxyoctane, and 1,2-epoxydecane.

11. The process of claim 7, wherein the polymerizing is carried out at a temperature of ~30° C. to 125° C.

12. The process of claim 7, wherein the polymerizing is carried for a time of 1 hour to 24 hours.

* * * * *